United States Patent [19]

Bostick et al.

[11] 4,263,406

[45] Apr. 21, 1981

[54] APPARATUS FOR CONTINUOUSLY REFERENCED ANALYSIS OF REACTIVE COMPONENTS IN SOLUTION

[75] Inventors: William D. Bostick; Mark S. Denton, both of Oak Ridge; Stanley R. Dinsmore, Norris, all of Tenn.

[73] Assignee: The United States of America as represented by the United States Department of Energy, Washington, D.C.

[21] Appl. No.: 62,375

[22] Filed: Jul. 31, 1979

[51] Int. Cl.³ ............................................. C12M 1/34
[52] U.S. Cl. .................................... 435/291; 435/808; 422/81
[58] Field of Search ....................... 435/17, 26, 4, 288, 435/291, 803, 808, 289; 422/81

[56] References Cited

U.S. PATENT DOCUMENTS 3,933,430  1/1976  Hare ....................................... 422/81

OTHER PUBLICATIONS

Schroeder; R. R. et al.; "Enzyme-Selective Detector Systems for High Pressure Liquid Chromatography", Jour. of Chromatography; vol. 134, pp. 83-90, (1977).
Schlabach; T. D. et al.; "A Continuous-Flow Enzyme Detector for Liquid Chromatography"; Journal of Chromatography; vol. 134, pp. 91-106, (1977).

Primary Examiner—Benoit Castel
Attorney, Agent, or Firm—Allen H. Uzzell; Stephen D. Hamel; C. Clay Carter

[57] ABSTRACT

A continuously referenced apparatus for measuring the concentration of a reactive chemical species in solution comprises in combination conduit means for introducing a sample solution, means for introducing one or more reactants into a sample solution, a reaction zone in fluid communication with said conduit means wherein a first chemical reaction occurs between said species and reactants, and a stream separator disposed within the conduit means for separating the sample solution into a sample stream and a reference stream. An enzymatic reactor is disposed in fluid communication with only the sample stream wherein a second reaction takes place between the said reactants, species, and reactor enzymes causing the consumption or production of an indicator species in just the sample stream. Measurement means such as a photometric system are disposed in communication with the sample and reference streams, and the outputs of the measurement means are compared to provide a blanked measurement of the concentration of indicator species. A peristaltic pump is provided to equalize flow through the apparatus by evacuation. The apparatus is particularly suitable for measurement of isoenzymes in body tissues or fluids.

9 Claims, 5 Drawing Figures

APPARATUS FOR CONTINUOUSLY REFERENCED ANALYSIS OF REACTIVE COMPONENTS IN SOLUTION

BACKGROUND OF THE INVENTION

1. Field of the Invention

This invention is related to the quantitative analysis of active species in solution. It is particularly useful for analyses of proteins in solutions containing interfering species, for example, effluent solutions from the ion exchange chromatographic separation of proteins. This invention is a result of a contract with the United States Department of Energy.

Separation of proteins by ion exchange chromatography is receiving considerable attention in the field of clinical diagnostics. Separation and analysis of isoenzymes (enzymes which catalyze the same reaction) have become important in diagnostic procedures with the discovery that various tissues express different isoenzyme contents. By monitoring isoenzyme concentration in serum one can identify tissue damage by a non-invasive method. For example, certain isoenzymes of creatine kinase (CK) and lactate dehydrogenase (LD) have molecular forms found predominantly in heart tissue. The quantitative analysis of creatine kinase and lactate dehydrogenase in body fluids such as serum can play a major role in the verification of myocardial infarction.

Lactate dehydrogenase activity is expressed by five isoenzymes, LD-1 through LD-5. Elevations in LD-1 and LD-2 suggest cardiac damage while elevations in LD-4 and LD-5 are indicative of hepatic or muscular damage. Three isoenzymes of creatine kinase have been identified; CK-MM, CK-MB, and CK-BB. The primary source of CK-MM, CK-MB, and CK-BB is, respectively, skeletal muscle, myocardium and smooth muscle. CK-MB has been reported to have a zero incidence of false negative and a reported specificity of 99% for myocardial infarction. See Wagner, G. S., et al, "The Importance of the Identification of the Myocardial-Specific Isoenzyme of Creatine Phosphokinase (MB form) in the Diagnosis of Acute Myocardial Infarction," *Circulation*, Vol. 47, p. 263 (1973). The elevation in concentration of CK-MB in serum is short-lived, however, rising acutely within the four hours after an infarction, peaking within 24 hours, and then returning to normal within 48 hours. Fortunately, an increase in the serum levels of LD-1 and LD-2 occurs about 12-24 hours after the onset of infarction symptoms and persists for days thereafter. Although lactate dehydrogenase isoenzymes are not as specific as CK-MB, for heart damage, the two assays taken in conjunction are confirmatory and virtually 100% diagnostic of myocardial infarction. The present invention is particularly useful for providing these and other diagnostic isoenzyme analyses.

2. Description of the Prior Art

In describing the work of others herein, we do not admit that such work is actually prior art under 35 USC 102 or 35 USC 103 or that the work was prior in time to the making of the invention described and claimed herein. We reserve the right to establish a date of conception and reduction to practice prior to the effective date of any publication or work herein described.

A number of writers have described the separation of isoenzymes by high performance chromatography and electrophoresis, see for example, Mercer, D. W., "Simultaneous Separation of Serum Creatine Kinase and Lactate Dehydrogenase Isoenzymes by Ion-Exchange Column Chromatography, "*Clinical Chemistry*, Vol. 21, No. 8, pp. 1102–1106 (1975). Selective photometric determination of isoenzymes in protein solutions has been impractical. Isoenzymes, as do most other proteins, absorb at 280 nm precluding selective or comparative absorption analyses in the presence of other proteins.

Schroeder, R. R., et al in "Enzyme-Selective Detector Systems for High-Pressure Liquid Chromatography," *Journal of Chromatography*, Vol. 134, pp. 83–90 (1977) proposed the use of a post column reaction zone in the analysis of chromatography effluents containing lactate dehydrogenase isoenzymes. In the Schroeder et al system a chromatographic column effluent was contacted with a solution containing lactate, nicotinamide adenine dinucleotide (NAD) and a buffer. This is the substrate for the reaction catalyzed by lactate dehydrogenase as follows:

In the Schroeder method the NADH (reduced form of NAD) is activated at 340 nm and fluoresces at 457 nm. Two embodiments were proposed. In one embodiment the substrate was added to the column effluent containing lactate dehydrogenase isoenzymes eluted with an NaCl gradient. The effluent stream was split into two segments and passed through respective delay coils (reaction zones), one maintained at 37° C. and one at 18° C. to permit the reactions to occur. The streams leaving the delay coils were each detected by a spectrofluorometer in an effort to provide blank correction. The system, however, was said to be unsatisfactory. Identical flow rates, critical to the blanking, could not be maintained in the split streams because of viscosity differences between the streams due to the different temperatures and to the NaCl gradient. In the second embodiment a substrate containing soluble enzymes was added to the column effluent and passed through two detection zones in series having a delay line (a reaction zone) in between to allow the production of detectable levels of NADH. The delay time between the detectors caused problems which included band spreading. The system was said to be capable of blanking only relatively pure samples not requiring large blank corrections. More complex samples such as human tissue specimens, serum or urine were said to require a computer program to perform matrix manipulation on the first detector output to provide blanking for the output of the second detector. The Schroeder system was also described by Toren, E. C., et al in Abstract 284 of *Clinical Chemistry*, Vol. 23, No. 6, p. 1172.

Another separation method for isoenzymes has been proposed by Chang, S. H. et al in "High Performance Liquid Chromatography of Proteins," *Journal of Chromatography*, Vol. 125, pp. 103–114 (1976). The chromatographic column effluent was mixed with soluble substrate and passed through a reaction bed containing an inert support material to permit the formation of spectrophotometrically detectable species. Difficulties could be encountered in the bed of inert material because of physical mixing of bands traveling through the packed column. The system contained no self-blanking apparatus. This application of a post-column reactor bed was also referred to in an abstract, Schlabach, T., et al, "Isoenzyme Analysis by H. P. L. C.," at the Tenth Annual Symposium on Advanced Analytical Concepts for the Clinical Laboratory, Paper No. 8. It can be appreciated from the limitations of the prior art that a simple, accurate, self-blanking system for the analysis of isoenzymes in complex solutions has long been needed.

STATEMENT OF THE OBJECTS

It is an object of this invention to provide an apparatus for analyzing active components such as isoenzymes in a mixture containing interfering components, where the analyses are not subject to the band spreading problems of the prior art.

It is another object to provide such an apparatus which employs a split stream without encountering problems of differential flow characteristics.

It is another object to provide a system which does not require complex electronic analysis or computer programs in order to provide blanking.

SUMMARY OF THE INVENTION

This invention is an apparatus for measuring the concentration of an active chemical species in solution comprising in combination: (a) conduit means for conducting a chromatographic separation effluent containing an active chemical species from a source of said effluent; (b) means for introducing enzymatic substrates and co-factors into said sample effluent; (c) a reaction zone disposed in fluid communication with said conduit means in which a first chemical reaction occurs involving said active species, enzymatic substrates and co-factors to produce an intermediate species; (d) a stream separator disposed within said conduit means for separating said effluent containing an active and intermediate species into a sample stream and a reference stream; (e) an enzymatic reactor with activator enzymes immobilized on a support disposed in fluid communication with said sample stream only, in which a second chemical reaction occurs between said intermediate and active chemical species and said activator enzymes to cause the consumption or production of an indicator species in said sample stream, in a concentration correlatable to the concentration of said active chemical species; (f) measurement means selected from the group consisting of photometric, amperometric and enthalpimetric devices, disposed in communication with said sample and reference streams, said means being sensitive to the concentration of said indicator species and thereby providing a measurement output for each of said sample and reference streams; (g) means for comparing the measurement output of said sample and reference streams to provide a blanked measurement of the concentration of said indicator species in said sample stream relative to said reference stream; and (h) a peristaltic pump for evacuating flow through said conduit means, reaction zone, stream separator, reactor, and measurement means.

The active chemical species can be catalytically active, causing a reaction to occur between introduced reactants, or the active species can be chemically reactive with the introduced reactants.

The source of solution to be measured can be an ion exchange column or other chromatographic separations apparatus. The reactor can be for example, an immobilized enzyme reactor preferably a microreactor, a catalytic reactor, an electrochemical cell, or a zone in which a non-interfering reactant is introduced. An inactive reactor can be disposed in fluid communication with the second sample stream (i.e., the reference stream) to provide duplicate flow characteristics. The measurement means can be a photometric means such as a referenced visible or ultraviolet spectrophotometer or a referenced fluorophotometer or other suitable apparatus such as an amperometric or enthalpimetric means.

DETAILED DESCRIPTION OF THE INVENTION

The apparatus of this invention is useful for measuring the concentration of virtually any species in solution which can be caused to participate in a reaction or reactions to ultimately yield or consume a quantitatively detectable indicator species. It is particularly useful in applications wherein direct measurements are impossible or impractical due to the presence of interfering species. As used herein, "interfering species" refers to chemical species which interfere with the concentration measurement technique used to detect the indicator species. For example, in photometric applications interfering species are species which absorb electromagnetic radiation in a frequency region at or near frequencies absorbed by the indicator species. In clinical applications the apparatus is useful for measuring body fluid proteins, such as isoenzymes.

In accordance with this invention a sample solution containing an active species is conducted from a source through a conduit wherein it is contacted with one or more reactants. The reactants may be added directly or generated in situ by adding appropriate precursors. The active species may be directly reactive with the reactants or it may be a catalyst such as an enzyme which causes a reaction to occur between reactants. The sample solution is separated by a stream separator into at least two sample streams. The first sample stream is passed into a reactor wherein a chemical reaction is caused to take place to produce or consume a detectable indicator species. The second sample stream, a reference, is not so reacted. Both first and second sample streams are measured by a suitable means, i.e., one sensitive to the concentration of the indicator species, to provide measurement outputs, e.g., electronic signals. The measurement ouput of the second (reference) sample stream is compared, e.g., subtracted, from that of the first sample stream, providing a continuously blanked measurement of the concentration of indicator species in the first sample stream. The concentration of the indicator species is a measure of the concentration of original active chemical species in the sample.

The apparatus of this invention is particularly adapted to the quantitative analysis of several components having similar properties, and which can each be reacted in the reactor to produce the same indicator species. The apparatus is particularly applicable to the analysis of isoenzymes in complex solutions. The isoenzymes can be first separated chromatographically, e.g., in a column, and the chromatographic effluent passed as a sample into the apparatus of this invention. Appropriate reactants are added to cause the ultimate production of indicator species in the reactor, whose concentration is correlatable (directly proportional or otherwise) to the concentration of active isoenzymes in the original sample solution. The separate isoenzymes produce the same indicator species. The sample stream leaving the reactor is measured for indicator concentration and the measurement is compared with that of an unreacted stream to provide a blanked measurement of the indicator species concentration. When the apparatus is used to measure components in a chromatographic column effluent in a continuous flow system, several chromatographically separated components can be measured sequentially when each generates the same indicator species. If different chromatographic effluent components react to produce indicator species absorbing at different wavelengths, the photometric means can be sensitive to several wavelengths of radiation.

Figure 1:
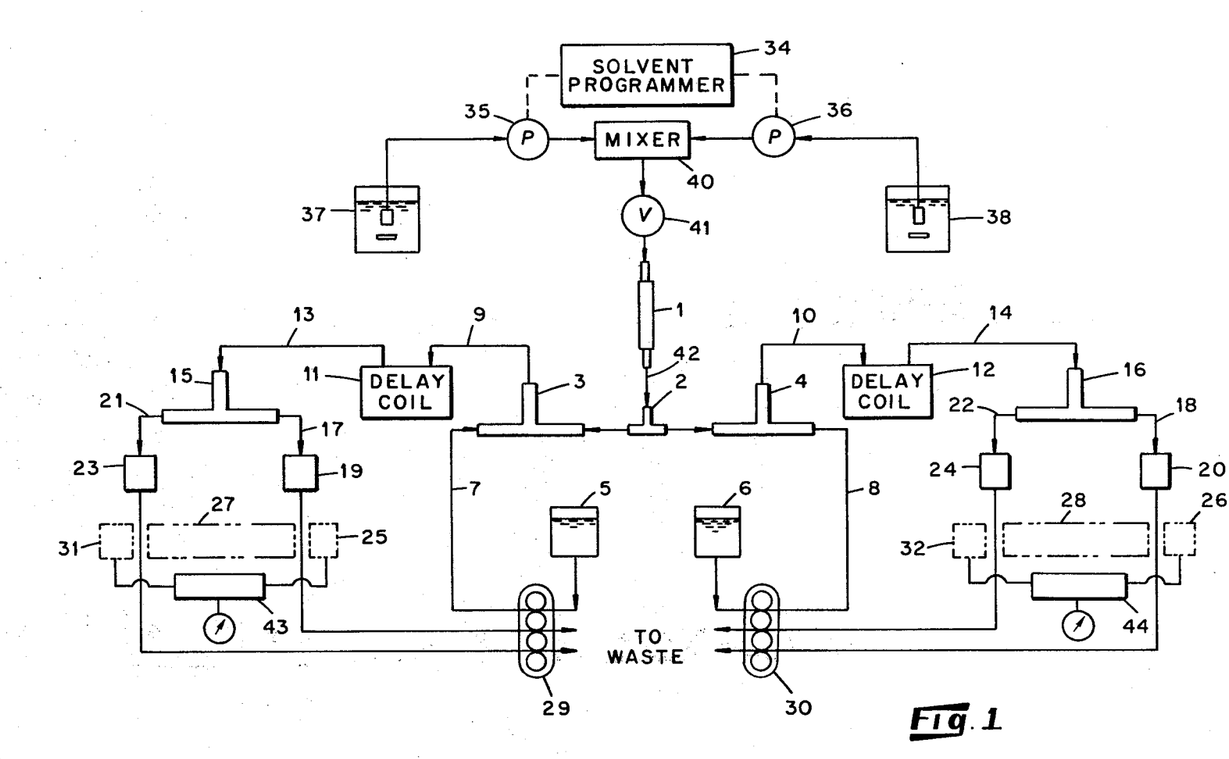
FIG. 1 is a schematic representation of an apparatus of this invention in combination with a chromatographic separation column and adapted for measuring two active components in the column effluent.

FIG. 1 is an embodiment of this invention in which two active chemical species can be measured. Effluent leaving chromatographic column 1 through line 42 is split by an effluent stream splitter 2 into two sample solutions, each going into one of the mixers 3 and 4. In each mixer the chromatographic effluent sample solution is mixed with a solution containing reactants from reservoirs 5 and 6 through lines 7 and 8. The addition of different substrates permits analysis of different active species downstream from the mixers. A chemical reaction, e.g., one catalyzed by the active species, occurs in lines 9 and 10 leaving the mixers as the stream passes through delay coils 11 and 12, which are reaction zones and can be, for example, coiled lengths of lines 9 and 10 in a water bath held at reaction temperature. In the delay coils a chemical reaction takes place involving the active species (catalytically or reactively) to produce a species which later reacts in the active reactors 19 and 20. Lines 13 and 14 from the delay coils carry the streams to stream splitters 15 and 16. The right effluents from the stream splitters (the first sample streams) pass through lines 17 and 18 to active reactors 19 and 20. The left effluents from stream splitters 15 and 16 (the second sample streams) pass through lines 21 and 22 to reference reactors 23 and 24. The active reactors can be, for example, immobilized enzymes or other catalysts, electrolytic cells, or zones in which a non-interfering reactant is introduced. In the active reactors, chemical reactions occur between one or more reactants from reservoirs 5 and 6 and one or more of the products produced in the delay coils, to produce (or consume) an indicator species. The reference reactors are inactive and are not essential. If reference reactors are used they should match the flow characteristics of the active reactors as closely as possible. In the reference reactors, conditions in the active reactors should be simulated as closely as possible without producing or consuming the indicator species. The effluents from the reference reactors and active reactors are passed through a stationary conventional referenced spectrophotometer wherein beams are passed from radiation sources 27 and 28 through the respective samples to sample beam detectors 25 and 26 and reference beam detectors 31 and 32. The outputs of the reference beam detectors 31 and 32 are compared with the outputs of sample beam detectors 25 and 26, respectively, in comparators 43 and 44 to provide a blanked measurement of the concentration of indicator species in the first sample stream. Peristaltic pumps 29 and 30 control the flow downstream of the chromatographic column. The column effluent results from a chromatographic separation (not a part of this invention) wherein different concentrations of an eluent are caused to pass through a column loaded with species to be detected. A solvent programmer 34 in combination with pumps 35 and 36 delivers flow from eluent reservoirs 37 and 38 having different concentrations to mixer 40 wherein they are combined according to a preselected schedule. Eluent samples are introduced through injector valve 41 to the chromatographic column 1.

The reactants entering from reservoirs 5 and 6 will of course depend upon the species being detected. The reactants can react, as shown in FIG. 1, during the passage through the system, i.e., in the delay coils, catalyzed by an active species. One or more of the resulting products are then reacted in the active reactors to provide the indicator species. Alternatively, reactants can be added from reservoirs 5 and 6 which themselves react with an active species to form indicator species upon passage through the active reactor. All that is necessary for the continuously blanking system of this invention is that a detectable indicator species be produced or consumed in one of the split sample streams in a concentration proportional or otherwise correlatable to the concentration of active component of interest in the column effluent. In this manner the reference beams and sample beams can be compared with the difference representing the concentration of the species formed in the active reactor. In some commercially available dual-channel referenced photometers, a single detector is used to measure both the reference and sample streams.

Figure 2:
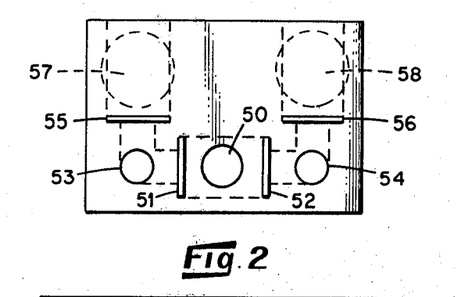
FIG. 2 depicts a referenced fluorophotometer configuration useful for performing fluorometric analyses according to this invention.

FIG. 2 depicts a referenced fluorophotometer arrangement which can be used instead of a spectrophotometer shown in FIG. 1. The source lamp 50 emits excitation radiation passing through excitation filters 51 and 52 to reference chamber 53 and sample chamber 54. The emissions from the chambers pass through emission filters 55 and 56 to photomultiplier tubes 57 and 58 to provide responses proportional to the fluorescing species. The intensity of the photomultiplier tubes response can be compared by conventional electronic means. The difference between the sample fluorescence and the reference fluorescence represents the blanked sample response. A non-referenced flow fluorometer and associated electronics are described in Thacker, L. H., "Improved Miniature Flow Fluorometer for Liquid Chromatography," J. Chromatogr. 136, pp. 213–220 (1977). The Thacker system can be readily adapted for use according to this invention by providing for conventional referencing detection and associated circuitry.

The analysis of catalytically active species is described in the following examples. Examples 1 and 2 are illustrated by correlation to the portion of the FIG. 1 system which analyzes the column effluent through stream splitter 2 towards mixer 4. If simultaneous analysis of two active components is desired, the appropriate substrates can be added to each of reservoirs 5 and 6.

EXAMPLE 1

Separation of Creatine Kinase Isoenzymes

A 30 cm high-pressure ion exchange column 1 slurry packed with DEAE-Glycophase CPG/250 from Corning Glass Works, Corning, New York, was contacted with serum samples from hospital patients referred for creatine kinase isoenzyme determination. The serum samples contained 1175 U/l total creatine kinase activity in a 72 microliter sample with and without 10 mM dithiothreitol (DTT). The serum samples were introduced through injector valve 41 (through an alternate route, not shown). Gradient elution was performed by a model 660 Solvent Programmer obtained from Waters Associates, Milford, Massachusetts, into Waters Model 6000A pumps 35 and 36. The flow through the 30 cm DEAE-Glychophase CPG/250 column was 42 ml/hr. The elution involved an initial five-minute hold at the concentration of solvent A from reservoir 37, 0.02 M NaCl+0.03 M tris(hydroxy methyl)methylamine buffer (TRIS), pH 7.4, followed by 0–100% solvent B from reservoir 38 at a number 4 gradient, i.e., a concave (%V vs. time) gradient standard on the Waters solvent programmer. Solvent B was 0.40 M NaCl+0.03 M TRIS, pH 7.4. The effluent from the column passed through the T-mixer 4 where it is combined with a substrate reagent at 4 ml/hr from reservoir 6, having the composition of the table.

TABLE

Substrate for Creatine Kinase Isoenzyme Analysis

|  | mmole/liter |
|---|---|
| creatine phosphate | 60 |
| glucose | 40 |
| adenosine diphosphate (ADP, a cofactor) | 4 |
| NADP | 4 |
| adenosine monophosphate (AMP, an inhibitor) | 10 |
| imidazole buffer (pH 6.7) | 200 |
| magnesium acetate (an activator) | 20 |
| dithiothreitol (an activator) | 10 |

The creatine phosphate and ADP in the substrate reagent are catalyzed by the creatine kinase isoenzymes in the eluate to produce creatine plus ATP during transport through the delay coil 12 maintained at about 37° C. with a fluid residence time of about 7 minutes. The effluent from the delay coil enters the stream splitter 16 wherein half the stream passes through line 18 to active microreactor 20 and half the stream passes through line 22 to inactive reference microreactor 24. The active microreactor contained indicator enzymes hexokinase (HK) and glucose-6-phosphate dehydrogenase (GPDH) co-immobilized on a beaded agarose. These enzymes linked the ATP produced in the delay coil to cause the production of ultraviolet-detectable NAD(P)H as follows:

The microreactors contained GPDH from Bakers' yeast which is specific for NADP+. If GPDH from *Leuconostoc mesenteroides* is used, NAD+ may be substituted for NADP+, thereby reducing the expense of the substrate and cofactor mixture. The reference microreactor, containing immobilized HK and GPDH on agarose, was deactivated by boiling. Both the active and the reference microreactors were 17 millimeters of 2 millimeter ID teflon tubing with a 10 micron pore size stainless steel frit. A silanized glass wool plug was installed at the downstream end to contain the packing. Co-immobilized GPDH and HK on agarose was obtained from Sigma Chemical Company. A slurry of the co-immobilized enzymes can be injected into the assembled microreactor by a syringe or Pasteur pipette. The streams leaving the microreactors were passed through the sample cell and reference cell respectively of a Waters Model 440 Dual Wavelength Absorbance Detector at 340 nm, and a blanked absorbance reading was obtained directly. The electrical conductivity (proportional to the salt content of the eluate) was measured downstream of the photometer. The conductivity tracks the elution gradient and need not be measured in ordinary practice.

Figure 3:
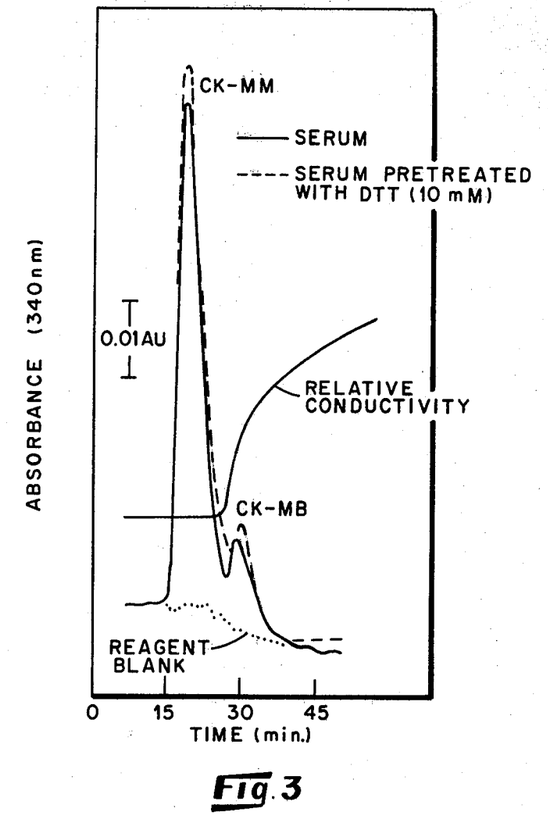
FIG. 3 is an absorbance curve of a continuously referenced analysis of creatine kinase in a serum sample according to this invention.
Figure 4:
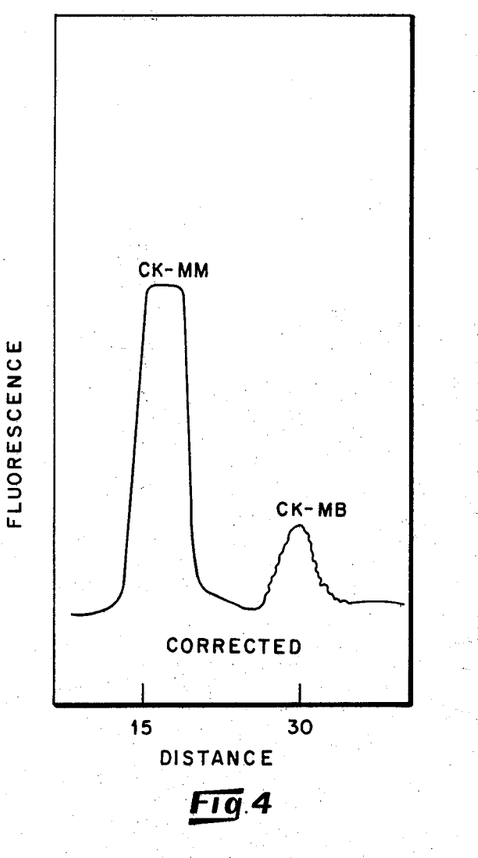
FIG. 4 is a fluorometric densitometry scan of a developed agarose electropherogram of the serum sample of FIG. 3.

FIG. 3 shows the blanked absorbance (in absorbance units) showing the two peaks corresponding to CK-MM and CK-MB. The absorbance of a reagent blank (substrate from reservoir 6) is also shown. FIG. 4 is a fluorometric densitometer scan of a developed agarose electropherogram of the serum sample of this example, confirming the presence of CK-MM and CK-MB.

EXAMPLE 2

Measurement of Lactate Dehydrogenase

Figure 5:
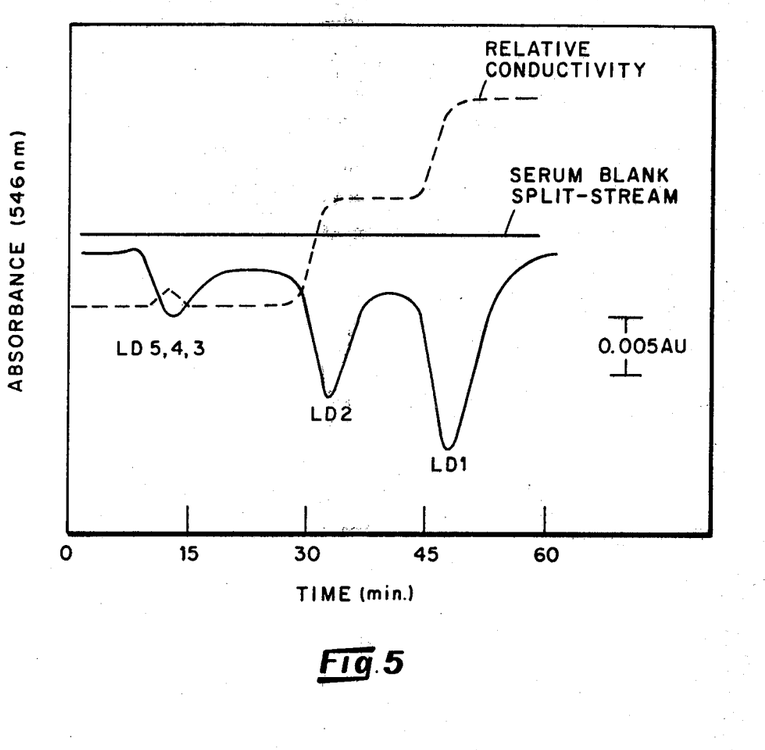
FIG. 5 is an absorbance curve of a continuously referenced analysis of serum lactate dehydrogenase according to this invention.

The chromatographic column 1 was loaded as in Example 1 with the serum sample. The LD isoenzymes were eluted by a step gradient rather than the programmed elution of Example 1. The step gradient was obtained by mixing portions of solution A, e.g., from reservoir 37 and solution B, e.g., from reservoir 38. The eluents consisted of (a) 63% B, or 0.076 M NaCl for 15 minutes; (b) 82% B, or 0.098 M NaCl for 15 minutes; and (c) 100% B, or 0.12 M NaCl for 15 minutes; wherein A is 0.03 M TRIS pH 8.0 and B is 0.012 M NaCl, 0.03 M TRIS, pH 8.0. The salt content of the eluent stream was monitored by means of a conductivity meter, located downstream of the sample cell of the absorbance detector as in Example 1. The substrate was prepared as follows: 0.5 M Li-l-lactate was mixed with 1.0 M 2-amino-2-methyl-1,3-propanediol buffer (2-AMP-diol). The pH was adjusted to 8.5 with acetic acid. NAD was added to 0.035 M and the pH was readjusted to 8.5, for final concentration of 50 mM lactate, 0.1 M buffer, and 3.5 mM NAD. A stock solution of 2,6-dichlorophenolindophenol (2,6-D) was made up separately at a concentration of 0.36 mg/ml. In the substrate, 2,6-D has a tendency to discolor over a period of several days. Consequently, 0.15 ml. of the 2,6-D solution was added per milliliter of reagent just prior to the run. The serum in the column was a 1:3 serum:saline solution of the serum used for the CK isoenzyme analysis of Example 1. The patient had an acute myocardial infarction. The results of the LD analyses are shown in FIG. 5. The LD-1 content is elevated relative to LD-2 as would be expected. The lactate dehydrogenase was detected by way of the following reactions:

The reaction was monitored at the maximum wavelength of the Waters detector (546 nm) for the disappearance of indicator 2,6-D (oxidized). The maximum absorbance for the oxidized indicator actually occurs at 600 hm. The diaphorase was immobilized on agarose in the active microreactor 20 via cyanogen bromide derivatization as described by Porath, J., et al "Preparation of Cyanogen Bromide-Activated Agarose Gels," J. Chromatogr. 86:53 (1973) which is incorporated herein by reference. The delay coil 12 had a residence time of 7 minutes.

EXAMPLE 3

Fluorometric Detection of CK Isoenzymes

In Example 1 above, the detection of chromatographically separated creatine kinase isoenzyme involved monitoring NAD(P)H produced in the active microreactor containing the appropriate indicator enzymes. NAD(P)H (and NADH) may be quantitated by absorbance at 340 nm or by their native fluorescence ($\lambda_{ex} \approx 340$ nm, $\lambda_{em} \approx 460$ nm). Although fewer constituents fluoresce after excitation at 340 nm than absorb light at this wavelength, thus imparting some degree of selectivity, there remain many endogenous fluorescent constituents in biological fluids which can interfere with the determination of NAD(P)H reaction product [see e.g., Aleyassine et al, Clin. Chem. 24, 492 (1978); Chuga et al, Clin. Chem. 24, 1286 (1978); Denton et al, Clin. Chem. 24, 1408 (1978); Bostick et al, Clin. Chem. 24, 1305 (1978)]. Although some investigators use unreferenced fluorescence to monitor NAD(P)H produced by enzymatic reactions [Schroeder et al, J. Chromatogr., 134, 83 (1977); Schlaback et al, J. Chromatogr., 134, 91 (1977); Schlabach and Regnier, J. Chromatogr., 158, 349 (1978)], response is not specific for this component.

FIG. 2 illustrates a flow-through referenced fluorometer, in which the fluorescence of a reference stream is subtracted from that of a sample stream. For the example of monitoring creatine kinase isoenzymes, the reaction product NAD(P)H is produced by the indicator enzymes in the active microreactor, as in Example 1. Fluorescent constituents endogenous to the sample will be common to both the sample and reference (unaltered) streams, thus their contribution to the overall fluorescence is easily compensated. Only the net difference in fluorescence (due to the NAD(P)H produced in the active microreactor interposed in the sample stream) is measured. This detection scheme adds significant specificity to the enhanced sensitivity of fluorescence monitoring. For NAD(P)H, fluorescence monitoring is typically 100 times as sensitive as absorbance measurement.

In another application of the invention polynuclear aromatic compounds (PNA's) whose metabolites are suspected carcinogens can be detected fluorometrically by using immobilized arylhydrocarbon hydroxylase, with or without epoxide hydrase, in the reactor. Those PNA's which are metabolized in the reactor (as shown by a difference in fluorescence between reference and sample streams) can be further tested for mutagenicity. For example, benzo(a)pyrene forms hydroxylbenzo(a)pyrene in the presence of arylhydrocarbon hydroxylaze.

As seen in the examples above, many enzymatic methods used in clinical diagnostics involve the cofactors NADH or NAD(P)H. In the example of the determination of lactate dehydrogenase (Example 2), diaphorase was used as an indicator enzyme, oxidizing NADH (produced in the primary reaction) to NAD while simultaneously reducing a colored dye. The change in optical property of the reduced dye reflected the original concentration of NADH and permitted continuously referenced on-line monitoring. The NADH produced in the primary reaction can also be electrochemically oxidized to NAD, directly producing a change in optical property.

Direct amperometric determination of NADH in complex biological matrices has not been feasible due to interference by other endogeneous electroactive constituents. Davis et al, in J. Liquid Chromatogr., 2, 663 (1979), were able to claim some selectivity for amperometric determination of NADH only after chromatographically separating this component from other electroactive constituents.

Unreferenced amperometry or photometry cannot produce a selective response for NADH, but the two techniques combined, with stream-splitting to produce an unaltered reference channel, greatly enhances selectivity. In the example of detection of lactate dehydrogenase isoenzymes, the reaction product NADH is electrochemically oxidized to NAD in the sample microreactor, resulting in a difference in optical property between sample and reference (unaltered) flow streams. In order to produce a response, the constituent must be electroactive at a given potential ($+0.75$ V vs. an Ag-/AgCl reference electrode) and have a significant difference in molar absorptivity between oxidized and reduced forms, e.g., near 340 nm. If even greater selectivity is required, fluoresence monitoring may be used, adding the further requirement that the constituent have significant fluorescence, e.g., near 460 nm. The combined restrictions yield a response very selective for NADH.

Amperometric monitoring may be made specific, providing a split-stream configuration is used and an active reactor is interposed in one arm of the split stream to alter the concentration of a specific electroactive constituent (e.g., as in the production of electroactive NAD(P)H in Example 1). Since there is only one electroactive constituent changed between the two channels, subtraction of signals yields a specific response.

An additional advantage of the use of immobilized enzyme microreactors is that the reactors can be removed from the system when not in use and stored under refrigeration, separately from the soluble reactants. We have found that such separate storage enhances the stability of both the enzymes and the reactant mixture. The immobilization of enzymes for use in a reactor according to this invention can be performed by any of the conventional methods in the art. See, for example, *Biotechnology and Bioengineering*, Vol. XVII, "High Performance Enzyme Reactors," pp. 1487–1491, John Wiley & Sons, Inc. (1978) and *Enzyme Engineering*, Vol. 2, Pye, E. K., et al, eds., pp. 67–76, "Review of Recent Enzyme Immobilization Techniques," Plenum Press, New York.

Based upon the description herein it will be apparent to those skilled in the art that any measurable property of the sample stream can be used to detect the presence of the indicator species generated or consumed in the active reactor and provide continuous referencing according to this invention. The apparatus of this invention can be modified in a suitable manner to analyze a wide variety of components by proper selection of reactants, reactors, and measurement procedures and such embodiments are contemplated as equivalents of those disclosed herein.

What is claimed is:

1. An apparatus for measuring the concentration of an active chemical species in solution comprising in combination:
   (a) conduit means for conducting a chromotographic separation effluent containing an active chemical species from a source of said effluent;
   (b) means for introducing enzymatic substrates and co-factors into said effluent;
   (c) a reaction zone disposed in fluid communication with said conduit means in which a first chemical reaction occurs involving said active species, enzymatic substrates, and co-factors to produce an intermediate species;
   (d) a stream separator disposed within said conduit means for separating said effluent containing an active and intermediate species into a sample stream and a reference stream, said stream separator being located downstream from said means for introducing;
   (e) an enzymatic reactor with activator enzymes immobilized on a support disposed in fluid communication with said sample stream only, in which a second chemical reaction occurs between said intermediate and active chemical species and said activator enzymes to cause the consumption or production of an indicator species in said sample stream, in a concentration correlatable to the concentration of said active species;
   (f) measurement means selected from the group consisting of photometric, amperometric and enthalpimetric devices, disposed in communication with said sample and reference streams, said means being sensitive to the concentration of said indicator species and thereby providing a measurement output for each of said sample and reference streams;
   (g) means for comparing the measurement output of said sample and reference streams to provide a blanked measurement of the concentration of said indicator species in said sample stream relative to said reference stream; and
   (h) a peristaltic pump for evacuating flow through said conduit means, reaction zone, stream separator, reactor, and measurement means.

2. The apparatus of claim 1 in which said reactor is a catalytic reactor.

3. The apparatus of claim 1 in which said reactor is an electrochemical cell.

4. The apparatus of claim 1 in which said reactor is a zone having means to introduce a non-interfering reactant to said sample stream.

5. The apparatus of claim 1 wherein said measurement means is an amperometric device.

6. The apparatus of claim 1 wherein said measurement means is an enthalpimetric device.

7. The apparatus of claim 1 in which said measurement means comprises photometric means which is a referenced spectrophotometer.

8. The apparatus of claim 1 in which said measurement means comprises photometric means which is a referenced flurophotometer.

9. The apparatus of claim 1 in which said measurement means comprises photometric means which is an ultraviolet spectrophotometer.

* * * * *